US012649923B2

(12) United States Patent
Kim et al.

(10) Patent No.: US 12,649,923 B2
(45) Date of Patent: Jun. 9, 2026

(54) COMPOSITION COMPRISING EMP3 INHIBITOR FOR INHIBITING GROWTH OF CANCER STEMCELL AND USE THEREOF

(71) Applicant: KOREA ATOMIC ENERGY RESEARCH INSTITUTE, Daejeon (KR)

(72) Inventors: In Gyu Kim, Daejeon (KR); Rae Kwon Kim, Sejong (KR); Yeon Jee Kahm, Hwaseong-si (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 1086 days.

(21) Appl. No.: 17/768,906

(22) PCT Filed: Oct. 14, 2020

(86) PCT No.: PCT/KR2020/014018
§ 371 (c)(1),
(2) Date: Apr. 14, 2022

(87) PCT Pub. No.: WO2021/075853
PCT Pub. Date: Apr. 22, 2021

(65) Prior Publication Data
US 2024/0102019 A1 Mar. 28, 2024

(30) Foreign Application Priority Data
Oct. 14, 2019 (KR) ........................ 10-2019-0127054

(51) Int. Cl.
*C12N 15/113* (2010.01)
*A61P 35/00* (2006.01)
*C07K 16/28* (2006.01)

(52) U.S. Cl.
CPC .......... *C12N 15/1138* (2013.01); *A61P 35/00* (2018.01); *C07K 16/28* (2013.01); *C07K 2317/76* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 9,617,545 | B2 | 4/2017 | Lee et al. |
| 10,604,568 | B2 | 3/2020 | Sahin et al. |
| 2016/0060634 | A1 | 3/2016 | Lee et al. |
| 2016/0159901 | A1 | 6/2016 | Sahin et al. |
| 2020/0385460 | A1 | 12/2020 | Sahin et al. |

FOREIGN PATENT DOCUMENTS

| | | |
|---|---|---|
| KR | 10-2016-0026624 A | 3/2016 |
| KR | 10-2016-0034417 A | 3/2016 |
| KR | 10-2016-0047735 A | 5/2016 |
| KR | 10-2018-0011707 A | 2/2018 |

OTHER PUBLICATIONS

Improving radiotherapy in cancer treatment: Promises and challenges. Oncotarget. 2017;8(37):62742-62758. Published Jun. 8, 2017) (Year: 2017).*
Ernst et al (Genomic and Expression Profiling of Glioblastoma Stem CellâLike Spheroid Cultures Identifies Novel Tumor-Relevant Genes Associated with Survival. Clin Cancer Res Nov. 1, 2009; 15 (21): 6541â6550) (Year: 2009).*
Hsieh et al. (Targeting EMP3 suppresses proliferation and invasion of hepatocellular carcinoma cells through inactivation of PI3K/Akt pathway. Oncotarget. 2015; 6(33): 34859-34874), (Year: 2015).*
Tomita et al (Aldehyde dehydrogenase 1A1 in stem cells and cancer. Oncotarget. 2016;7(10):11018-11032), (Year: 2016).*
Selecting targets for cancer prevention: where do we go from here ?. Nat Rev Cancer 6, 867-874; 2006 (Year: 2006).*
Jia et al (Constructing the boundary between potent and ineffective siRNAs by MG-algorithm with C-features. BMC Bioinformatics. Aug. 13, 2022;23(1):337) (Year: 2022).*
Hattab et al (Clinical Advances of siRNA-Based Nanotherapeutics for Cancer Treatment. Pharmaceutics. Jul. 2, 2021;13(7):1009) (Year: 2021).*
Oh (siRNA delivery systems for cancer treatment; Advanced Drug Delivery Reviews 61 (2009) 850-86) (Year: 2009).*
Almagro & Fransson, Frontiers in Bioscience 2008; 13:1619-33; (Year: 2018).*
Gershoni et al., Epitope Mapping, Biodrugs 2007; 21 (3): 145-156 p. 146 section 1.1). (Year: 2007).*
Blythe et al., Benchmarking B cell epitope prediction: Underperformance of existing methods, Protein Science (2005), 14:246-248 p. 246) . (Year: 2005).*
Schreiber et al.,3D-Epitope-Explorer (3DEX): Localization of Conformational Epitopes within Three-Dimensional Structures of Proteins, Wiley Interscience, 2005 42-44, 60596, p. 879). (Year: 2005).*
Hanahan D et al. Cell 2011 144(5) p. 646-674, (Year: 2011).*
Lee KW et al. Nature Reviews Cancer 2011 11 211-218, p. 211 (Year: 2011).*
Lichtman MA et al. The Oncologistâ2017; 22(5); 542â548 (Year: 2017).*
International Search Report issued on Jan. 21, 2021, for corresponding International Patent Application No. PCT/KR2020/014018.

(Continued)

*Primary Examiner* — Zachariah Lucas
*Assistant Examiner* — Sarah A Alsomairy
(74) *Attorney, Agent, or Firm* — Hauptman Ham, LLP

(57) ABSTRACT

The present invention relates to a composition for inhibiting the growth of cancer stem cells and a use thereof. When treated with the EMP3 inhibitor, cancer stem cells expressing ALDH1 decrease in self-renewal potential, invasiveness, and migration ability and thus are restrained from growing, whereby cancer having stemness properties, which are resistant to conventional anticancer therapies, can be effectively treated.

10 Claims, 12 Drawing Sheets

Specification includes a Sequence Listing.

(56) References Cited

OTHER PUBLICATIONS

Written Opinion issued on Jan. 21, 2021, for corresponding International Patent Application No. PCT/KR2020/014018.

Mechthild Krause et al., "Cancer stem cells: Radioresistance, prediction of radiotherapy outcome and speci!c targets for combined treatments," Advanced Drug Delivery Reviews, 2017, vol. 109, pp. 63-73, available online Feb. 12, 2016; cited in NPL Nos. 1 and 2.

Dominique Bonnet et al., "Human acute myeloid leukemia is organized as a hierarchy that originates from a primitive hematopoietic cell," Nature Medicine, Jul. 1997, vol. 3, No. 7, pp. 730-737.

Monya Baker, "Melanoma in mice casts doubt on scarcity of cancer stem cells," Nature, Dec. 4, 2008, vol. 456, p. 553.

Adam Nagy et al., "Validation of miRNA prognostic power in hepatocellular carcinoma using expression data of independent datasets," Scientific Reports, 2018, vol. 8, article No. 9227, published online Jun. 15, 2018.

Muhammad W. Akbar, "Characterization of chemosensitivity proles of breast cancer cell lines, with and without stem cell like features," Master's thesis, Bilkent university, Aug. 2014, pp. 1-107 (See abstract; pp. 2, 5, 25, 38, and 73-74; table 5.1; and figures 5 and 10); cited in NPL Nos. 1 and 2.

Xiao Chun Hong et al., "Epithelial membrane protein 3 functions as an oncogene and is regulated by microRNA-765 in primary breast carcinoma," Molecular Medicine Reports, 2015, vol. 12, pp. 6445-6450; cited in NPL Nos. 1 and 2.

Tomohiko Sakabe et al., "Expression of Cancer Stem Cell-associated DKK1 mRNA Serves as Prognostic Marker for Hepatocellular Carcinoma," Anticancer Research, 2017, vol. 37, pp. 4881-4888; cited in NPL No. 1.

Anne T. Collins et al., "Prospective Identification of Tumorigenic Prostate Cancer Stem Cells," Cancer Research, Dec. 1, 2005, vol. 65, pp. 10946-10951.

John E. Dick, "Breast cancer stem cells revealed," PNAS, Apr. 1, 2003, vol. 100, No. 7, pp. 3547-3549.

Roxanne Khamsi, "Cancer stem cells produce brain tumours," Nature, Nov. 17, 2004 (DOI https://doi.org/10.1038/news041115-10).

Lucia Ricci-Vitiani et al., "Identification and expansion of human colon-cancer-initiating cells," Nature Letters, Jan. 4, 2007, vol. 445, pp. 111-115.

Liu et al., "Cancer stem cells and their niche in cancer progression and therapy", Cancer Cell International, Dec. 1, 2023, 23:305, 12 pages.

Marzagalli et al., "Cancer Stem Cells—Key Players in Tumor Relapse", Cancers, Jan. 20, 2021, 13, 376, 22 pages.

* cited by examiner

| GeneName | Normalized | Raw | Control |
|---|---|---|---|
| epithelial membrane protein 3 | 14.749069 | 7438.16 | 5041.5483 |

COMPOSITION COMPRISING EMP3 INHIBITOR FOR INHIBITING GROWTH OF CANCER STEMCELL AND USE THEREOF

CROSS-REFERENCE TO RELATED APPLICATIONS

The application is a national phase of PCT/KR2020/014018 filed on Oct. 14, 2020, which is based on and claims priority to Korean Patent Application No. 10-2019-0127054 filed on Oct. 14, 2019, which are incorporated herein by reference in their entireties.

TECHNICAL FIELD

The present invention relates to a composition for inhibiting the growth of cancer stem cells, and a use thereof.

BACKGROUND ART

Similar to normal stem cells present in normal cells, about 1% to 2% of cancer stem cells are present in cancer tissue. The cancer stem cells were revealed to be present in leukemia by Dr. John E. Dick in 1997 (Nat Med, 1997), and subsequently, the presence of cancer stem cells was also reported in breast cancer (PNAS, 2003), brain tumor (Nature, 2004), prostate cancer (Cancer Res, 2005), colorectal cancer (Nature, 2007), and melanoma (Nature, 2008). Such cancer stem cells have self-renewal potential, which is a property of normal stem cells, and thus can cause cancer-related cells, which have been reduced or disappeared by an anticancer treatment, to self-renew, thereby causing cancer to recur. Moreover, such cancer stem cells have migration and invasion ability and thus can cause cancer metastasis. Due to the aforementioned properties of the cancer stem cells, the cancer stem cells have significantly emerged as a major cause of malignant transformation of cancer, resistance to an anticancer treatment, and cancer metastasis.

In the case of normal stem cells, the growth and differentiation of cells are regulated by a tightly regulated self-renewal mechanism, whereas cancer stem cells are affected by tumor microenvironmental factors around cancer cells to cause abnormal self-renewal and differentiation, and, due to such a phenomenon, can acquire resistance to anticancer treatments such as a radiation treatment and chemotherapy with anticancer drugs, and can cause cancer metastasis and recurrence.

Despite the high need to target and treat cancer stem cells for an anticancer treatment, since most of the anticancer drugs currently on the market act with a mechanism to inhibit known target genes in cancer cells or to inhibit cancer-related cell signaling in cancer cells, anticancer drugs that act with such a mechanism have difficulties in being applied to anticancer treatments due to mutations in cancer-related genes or proteins and complex cell signaling. Therefore, in order to increase the therapeutic effect and survival rate of cancer patients, a therapeutic method targeting cancer stem cells is required.

DISCLOSURE OF THE INVENTION

Technical Problem

The present inventors have studied a technique for treating cancer having anticancer treatment-resistant cancer stem cell properties, and have confirmed that the expression level of epithelial membrane protein 3 (EMP3) is related to the properties of cancer stem cells, thereby completing the present invention.

Accordingly, an object of the present invention is to provide: a composition which is for inhibiting the growth of cancer stem cells and can be used to significantly improve the therapeutic effect on cancer through inhibition of self-renewal, inhibition of invasion, and inhibition of metastasis of cancer-related cells; a pharmaceutical composition for preventing or treating cancer; and a composition for assisting a radiation anticancer treatment.

Technical Solution

In order to achieve the object, the present invention provides a composition for inhibiting the growth of cancer stem cells, the composition containing an epithelial membrane protein 3 (EMP3) inhibitor as an active ingredient.

Moreover, the present invention provides a pharmaceutical composition for preventing or treating cancer having ALDH1-overexpressing cancer stem cell properties, the pharmaceutical composition containing an epithelial membrane protein 3 (EMP3) inhibitor as an active ingredient.

Further, the present invention provides a composition for assisting a radiation anticancer treatment, the composition containing an epithelial membrane protein 3 (EMP3) inhibitor as an active ingredient.

Furthermore, the present invention provides a method for inhibiting the growth of cancer stem cells, a method for preventing or treating cancer having cancer stem cell properties, and/or a method for enhancing the sensitivity of cancer cells to radiation, the methods including a step for inhibiting the expression or activity of an epithelial membrane protein 3 (EMP3) in a subject.

In addition, the present invention provides: an epithelial membrane protein 3 (EMP3) inhibitor for use in inhibiting the growth of cancer stem cells; an epithelial membrane protein 3 (EMP3) inhibitor for use in preventing or treating cancer having cancer stem cell properties; and/or an epithelial membrane protein 3 (EMP3) inhibitor for use in enhancing the sensitivity of cancer cells to radiation.

Advantageous Effects

According to the composition of the present invention, when treated with the EMP3 inhibitor, cancer stem cells expressing ALDH1 decrease in self-renewal potential, invasiveness, and migration ability and thus are restrained from growing, whereby cancer having cancer stem cell properties, which are resistant to conventional anticancer therapies, can be effectively treated.

Moreover, the present invention is a technique in which by the concurrent treatment with conventional anticancer drugs or radiation treatments, anticancer activity can be further increased and the used amount of anticancer drugs can be drastically reduced, and thus the side effects caused by the use of anticancer drugs can be reduced and the effect of a radiation anticancer treatment on subjects who are difficult to treat due to resistance to conventional radiation treatments can be significantly improved, and the technique is useful for an effective treatment of cancer having cancer stem cell properties, which have poor prognoses for conventional anticancer treatments.

MODE FOR CARRYING OUT THE INVENTION

Figure 1:
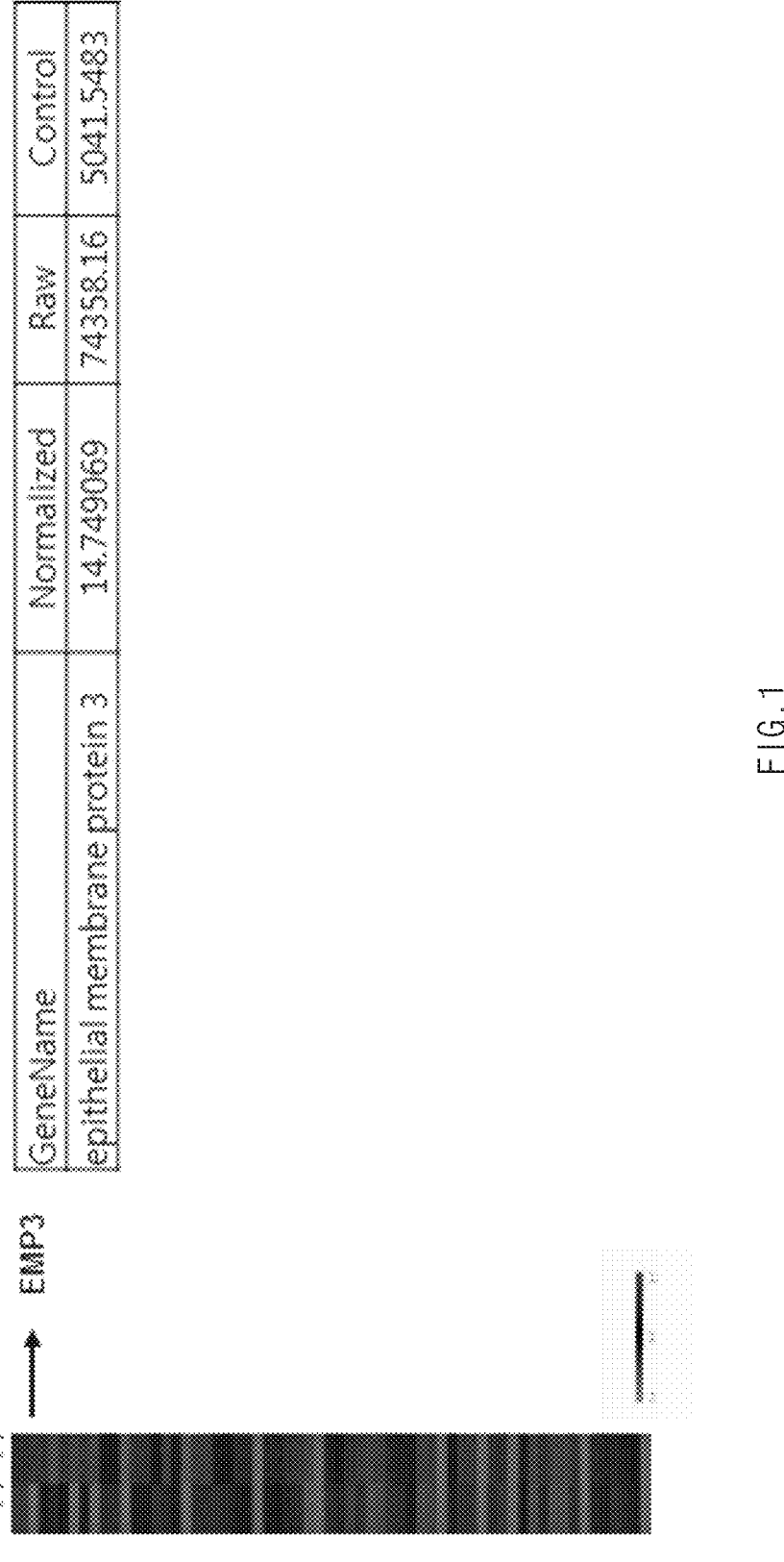
FIG. 1 shows the results of checking the difference in expression of EMP3 in ALDH1-positive cells and ALDH1-negative cells using a microarray.

Hereinafter, the present invention will be described in detail.

In one aspect, the present invention provides a composition for inhibiting the growth of cancer stem cells, the composition containing an epithelial membrane protein 3 (EMP3) inhibitor as an active ingredient.

The "cancer stem cell (CSC)" in the present invention refers to an undifferentiated cell having the ability to differentiate into various cancer cells. Cancer stem cells are present in a ratio of about 1% to 2% in malignant tumor tissue, have self-replication ability and pluripotency, which are properties of normal stem cells, but have abnormal self-regulatory functions, and thus the number of cells increases due to cell division activation, and cancer stem cells differentiate themselves into malignant tumor cells. It is known that due to such properties of cancer stem cells, general cancer cells are removed through an anticancer treatment, but cancer stem cells survive, and cancer recurrence and metastasis are caused by some of the surviving cancer stem cells.

Specifically, the cancer stem cells according to the present invention may be cancer cells in which aldehyde dehydrogenase 1 (ALDH1) protein, which is one of the markers of cancer stem cells, is overexpressed or the activity of the protein is positive.

The "epithelial membrane protein 3 (EMP3)" in the present specification is a member of the peripheral myelin gene family, and is a transmembrane protein involved in cell-cell interaction and cell proliferation. The detailed functions and mechanisms of EMP3 are not known.

In the present invention, it was confirmed that EMP3 selectively inhibits cancer stem cells expressing a specific marker, and in particular, kills a cancer cell group including cancer stem cells with high resistance to an anticancer treatment, and thus an excellent anticancer effect can be achieved.

In an exemplary embodiment, it was confirmed that cancer cells were classified into cancer stem cells and normal cancer cells, and EMP3 was expressed at a high level in the classified cancer stem cells.

In an exemplary embodiment, it was confirmed that when EMP3 was inhibited in order to check the correlation of EMP3 inhibition with the change in the adhesion ability of cancer stem cells to the extracellular matrix, the adhesion ability to the extracellular matrix was significantly reduced.

In an exemplary embodiment, it was confirmed that when EMP3 was inhibited in order to confirm the correlation of EMP3 inhibition with the change in the renewal potential of cancer stem cells, the ability to form cancer stem cells was reduced, and sox2 and oct4, which are involved in the renewal potential of the cancer stem cells, were reduced.

In an exemplary embodiment, it was confirmed that when EMP3 was inhibited in order to confirm the correlation of EMP3 inhibition with the change in metastasis of cells, that is, the change in migration and invasion ability, the invasiveness and migration ability were significantly reduced.

In an exemplary embodiment, it was confirmed that when EMP3 was inhibited in order to confirm the correlation of EMP3 inhibition with the resistance to a radiation treatment, a small colony of cells surviving after irradiation with radiation was formed.

The term "EMP3 inhibitor" in the present invention is used to collectively refer to all substances that reduce the expression or activity of EMP3, and specifically include all formulations that reduce the expression level or activity of EMP3 by reducing the expression of EMP3 at the transcriptional level or interfering with the activity of EMP3, through a method such as acting directly on EMP3 or acting indirectly on a ligand thereof.

The EMP3 inhibitor can be used without limitation on the form thereof, such as a compound, a nucleic acid, a peptide, a virus, or a vector containing the nucleic acid, which can target EMP3 to inhibit the expression or activity of EMP3. The EMP3 inhibitor is not limited to these examples, but may be specifically an oligonucleotide which inhibits the expression of EMP3 mRNA, or an antibody, which inhibits the activity of EMP3 protein or a ligand protein for EMP3, or an antigen-binding fragment thereof, and more specifically, the oligonucleotide acting on EMP3 mRNA may be an antisense oligonucleotide, an aptamer, shRNA, or siRNA, which is specific for EMP3 mRNA.

The term "antisense oligonucleotide" in the present invention is DNA, RNA, or a derivative thereof containing a nucleic acid sequence that is complementary to the sequence of a specific mRNA, and the antisense oligonucleotide binds to a complementary sequence in mRNA and acts to inhibit the translation of mRNA into a protein. The antisense oligonucleotide sequence refers to a DNA or RNA sequence that is complementary to the EMP3 mRNA and capable of binding to the mRNA. The sequence can inhibit the essential activity for translation of the EMP3 mRNA, translocation into the cytoplasm, maturation, or all other overall biological functions. The length of the antisense oligonucleotide may be 6 to 100 bases, preferably 8 to 60 bases, and more preferably 10 to 40 bases. The antisense oligonucleotide can be synthesized in vitro by a conventional method and administered in vivo, or the antisense oligonucleotide can be synthesized in vivo. One example of synthesizing the antisense oligonucleotide in vitro is using RNA polymerase I. One example of allowing antisense RNA to be synthesized in vivo is allowing antisense RNA to be transcribed by using a vector with the origin of a multiple cloning site (MCS) in the opposite direction. It is preferable that the antisense RNA is not translated into a peptide sequence by allowing a translation stop codon to be present in the sequence thereof. The design of the antisense oligonucleotide, which can be used in the present invention, can be made according to a method known in the art with reference to the base sequence of EMP3.

The term "aptamer" in the present invention is a single-stranded oligonucleotide, and refers to a nucleic acid molecule having a size of about 20 to 60 nucleotides and having binding activity to a predetermined target molecule. The aptamer has various three-dimensional structures according to the sequence, and can have high affinity with a specific substance, like an antigen-antibody reaction. The aptamer can inhibit the activity of a predetermined target molecule by binding to the predetermined target molecule. The aptamer according to the present invention may be RNA, DNA, a modified nucleic acid, or a mixture thereof, and may be in a linear or cyclic form. Preferably, the aptamer can play a role in inhibiting the activity of EMP3 by binding to EMP3. Such an aptamer can be produced from the sequence of EMP3 by a person with ordinary skill in the art through a known method.

The term "siRNA" or "shRNA" in the present invention is a nucleic acid molecule capable of mediating RNA interference or gene silencing, and can suppress the expression of a target gene, and is thus used in an efficient gene knockdown method or gene therapy method. shRNA is a single-stranded oligonucleotide in which a hairpin structure is formed through binding between complementary sequences, and the shRNA is cleaved by a dicer in vivo to become siRNA, which is a double-stranded oligonucleotide and is a small RNA fragment having a size of 21 to 25 nucleotides, and can specifically bind to mRNA having a complementary sequence to thereby inhibit the expression thereof. Therefore, which means of shRNA and siRNA to be used can be determined through the selection of a person with ordinary skill in the art, and if mRNA sequences targeted by shRNA and siRNA are the same, a similar expression reduction effect can be expected. For the purposes of the present invention, shRNA and siRNA can inhibit EMP3 by specifically acting on EMP3 and cleaving EMP3 mRNA molecules to induce an RNA interference (RNAi) phenomenon. siRNA can be chemically or enzymologically synthesized. A method for producing siRNA is not particularly limited, and methods known in the art can be used. For example, there are a method for directly chemically synthesizing siRNA, a method for synthesizing siRNA using in vitro transcription, a method for cleaving, using an enzyme, long double-stranded RNA synthesized by in vitro transcription, an expression method through intracellular delivery of an shRNA-expressing plasmid or a viral vector, an expression method through intracellular delivery of a polymerase chain reaction (PCR)-induced siRNA expression cassette, and the like, but the method for producing siRNA is not limited to these examples.

Specifically, siRNA for EMP3 according to the present invention may consist of a double strand of the oligonucleotide of SEQ ID NO: 2 and an oligonucleotide having a complementary sequence thereto, but is not limited thereto.

Moreover, the oligonucleotide of SEQ ID NO: 2 includes an oligonucleotide including substantially the same base sequence as that of the oligonucleotide of SEQ ID NO: 2 or SEQ ID NO: 3. The oligonucleotide including substantially the same base sequence refers to an oligonucleotide including a base sequence having a sequence homology of 75% or greater, 80% or greater, or 95% or greater to the base sequence of SEQ ID NO: 2 or SEQ ID NO: 3.

TABLE 1

| Gene | Direction | siRNA Sequence Information (5'->3') | SEQ ID NO: |
|------|-----------|--------------------------------------|------------|
| EMP3 | Forward direction | CUG CUU UUC GUG GCC ACU U | 2 |
|      | Reverse direction | AAG UGG CCA CGA AAA GCA G | 3 |

The term "antibody" in the present invention refers to a substance that reacts to an antigen, which is an external substance, when the antigen invades while circulating in blood or lymph in the immune system of a living body, and is a globulin-based protein formed in lymphoid tissue and also called an immunoglobulin. The antibody is a protein produced by B cells and flowing into body fluids, and specifically binds to an antigen, one antibody molecule has two heavy chains and two light chains, and each heavy chain and each light chain have a variable region at an N-terminal end thereof. Each variable region consists of three complementarity determining regions (CDRs) and four framework regions (FRs), and the complementarity determining regions determine the antigen-binding specificity of an antibody, and are present as relatively short peptide sequences maintained by framework regions of the variable region.

For the purposes of the present invention, the antibody may be an antibody capable of inhibiting the activity of EMP3 by binding to EMP3 or a ligand protein of EMP3.

The term "ligand" in the present invention refers to a substance that forms a complex with a biomolecule to bring about a biological reaction, and the "ligand protein of EMP3" or "ligand protein for EMP3" may be a protein that binds to EMP3 to thereby activate EMP3 or increase the activity of EMP3.

Specifically, the antibody against EMP3 according to the present invention may be a polypeptide that binds to the amino acid sequence of SEQ ID NO: 4, but is not limited thereto.

Moreover, the polypeptide binding to the amino acid sequence of SEQ ID NO: 4 includes a polypeptide, which has substantially the same amino acid sequence as that of the polypeptide binding to the amino acid sequence of SEQ ID NO: 4, and a mutant thereof or an active fragment thereof. The polypeptide having substantially the same amino acid sequence refers to a polypeptide including an amino acid sequence having a sequence homology of 75% or greater, 80% or greater, 90% or greater, or 95% or greater to the polypeptide binding to the amino acid sequence of SEQ ID NO: 4.

TABLE 2

| Protein Name | EMP3 Immunogen Sequence | SEQ ID NO: |
|---|---|---|
| EMP3 | DKSWWTLPGKESLNLWYDCTWNNDTKTWACSN VSENGWLKA | 4 |

As described above, the EMP3 inhibitors can inhibit the growth of cancer stem cells by reducing the self-renewal potential, invasiveness, and migration ability of the cancer stem cells.

In addition, the present invention provides a method for inhibiting the growth of cancer stem cells, the method including a step for inhibiting the expression or activity of an epithelial membrane protein 3 (EMP3) in a subject.

Specifically, the method for inhibiting the growth of cancer stem cells can be carried out by administering an EMP3 inhibitor to a subject.

The "subject" may include a human. Moreover, the term "subject" may be a subject in need of administration of the EMP3 inhibitor of the present application, and the subject in need of the administration may include not only a subject who has been diagnosed with a related disease and a subject who has developed a related symptom, but also a subject who wants administration to prevent the development of a disease or symptom or to improve health. For example, the subject in need of the administration may be a subject who has developed resistance to conventional anticancer drugs, or the like.

Furthermore, the present invention provides an epithelial membrane protein 3 (EMP3) inhibitor for use in inhibiting the growth of cancer stem cells.

In another aspect, the present invention provides a composition for preventing or treating cancer having cancer stem cell properties, the composition containing an epithelial membrane protein 3 (EMP3) inhibitor as an active ingredient.

The cancer having cancer stem cell properties shows resistance to conventional anticancer treatments and has a poor prognosis, and thus a treatment different from the conventional anticancer treatments should be applied. For example, even in patients with the same carcinoma, the patient with the carcinoma having a high ratio of cancer stem cells will not be able to obtain a cancer therapeutic effect through conventionally known anticancer treatments such as administration of anticancer drugs and a radiation treatment. Therefore, even with the same type of cancer, when the ratio of cancer stem cells in the cells at a cancer lesion site is high, it is very important to apply a novel treatment method different from conventional anticancer treatments.

The "cancer having cancer stem cell properties" in the present invention refers to cancer with a high proportion of cancer stem cells in a cell group constituting cancer. Considering that the proportion of cancer stem cells in general cancer cells is about 1% or greater and less than 5%, for example, a case in which the proportion of cancer stem cells in a cell group constituting cancer is 5% or greater, 10% or greater, 30% or greater, 50% or greater, or 70% or greater can be defined as "cancer having cancer stem cell properties", and, as described above, the cancer having cancer stem cell properties can be characterized by showing resistance to conventional anticancer treatments and having a poor prognosis for the anticancer treatments.

Specifically, the "cancer having cancer stem cell properties" in the present invention may be cancer that overexpresses ALDH1. The cancer overexpressing ALDH1 may be cancer with a relatively higher proportion of cancer stem cells, in which ALDH1 is expressed or the activity thereof is positive, compared to general cancer.

Specifically, the "cancer overexpressing ALDH1" may be one or more selected from the group consisting of lung cancer, breast cancer, liver cancer, kidney cancer, gastric cancer, pancreatic cancer, and brain cancer, but is not limited to these examples.

In an exemplary embodiment, the present inventors distinguished and sorted ALDH1-activated cells and ALDH1-inactivated cells, and confirmed that the expression levels of EMP3 were increased in the ALDH1-activated cells. Moreover, in an exemplary embodiment, the present inventors confirmed that cancer stem cells having ALDH1 activity were a major factor in cancer growth, from the decrease in the self-renewal potential, growth ability, invasiveness, and migration ability of lung cancer stem cells when ALDH1-activated lung cancer cells were treated with an EMP3 inhibitor.

In the composition for preventing or treating cancer having cancer stem cell properties according to the present invention, the details of the EMP3 and the EMP3 inhibitor are as described above.

The prevention or treatment of cancer may be to prevent cancer chemoresistance, cancer recurrence, or cancer metastasis during or after a cancer treatment, through reducing self-renewal potential, growth ability, invasiveness, and migration ability of cancer stem cells.

When the composition for preventing or treating cancer of the present application is used as a pharmaceutical composition, the pharmaceutical composition may further contain a pharmaceutically acceptable carrier or additive, in addition to the EMP3 inhibitor.

The "pharmaceutically acceptable" means that the substance does not inhibit the activity of the active ingredient and does not have toxicity beyond what an application (prescription) target is adaptable to, and the "carrier" is defined as a compound that facilitates the addition of a compound into cells or tissue.

The pharmaceutical composition according to the present invention may be administered alone or in the form of a mixture with any convenient carrier or the like, and such an administration dosage form may be a single-administration or repeated-administration dosage form. The pharmaceutical composition may be a solid formulation or a liquid formulation. The solid formulation includes a powdered drug, a granule, a tablet, a capsule, a suppository, and the like, but is not limited to these examples. The solid formulation may contain a carrier, a flavoring agent, a binding agent, a preservative, a disintegrating agent, a lubricant, a filler, and the like, but is not limited thereto. The liquid formulation includes water, a solution agent such as a propylene glycol solution, a suspension, an emulsion, and the like, but is not limited to these examples, and can be produced by adding an appropriate colorant, flavoring agent, stabilizing agent, or viscosity-increasing agent. For example, the powdered drug can be produced by simply mixing a tri-hydroxy derivative of a polyunsaturated fatty acid, which is the active ingredient of the present invention, and an appropriate pharmaceutically acceptable carrier such as lactose, starch, or microcrystalline cellulose. The granule can be produced by mixing the tri-hydroxy derivative of the polyunsaturated fatty acid of the present invention, an appropriate pharmaceutically acceptable carrier, and an appropriate pharmaceutically acceptable binding agent such as polyvinylpyrrolidone and hydroxypropyl cellulose, and then using a wet granulation method using a solvent such as water, ethanol, or isopropanol, or a dry granulation method using a compressive force. Moreover, the tablet can be produced by mixing the aforementioned granule and an appropriate pharmaceutically acceptable lubricant such as magnesium stearate, and then tableting the mixture using a tableting machine.

The pharmaceutical composition may be administered as an oral agent, an injection (for example, an intramuscular injection, an intraperitoneal injection, an intravenous injection, an infusion, a subcutaneous injection, and an implant), an inhalant, a nasal administration agent, a vaginal agent, a rectal administration agent, a sublingual agent, a transdermal agent, a topical agent, or the like, depending on the disease to be treated and the conditions of a subject, but is not limited thereto. The pharmaceutical composition can be formulated into an appropriate administration unit dosage form, which is typically used and non-toxic and contains a pharmaceutically acceptable carrier, additive, and vehicle, according to the route of administration.

The pharmaceutical composition may be administered in an amount of about 0.0001 mg/kg to about 10 g/kg daily, and may be administered in a daily dosage of about 0.001 mg/kg to about 1 g/kg. However, the dosage may vary depending on the degree of purification of the mixture, the conditions (age, sex, body weight, and the like) of a patient, the severity of the condition being treated, and the like. The total daily dose may be administered in several divided doses during the day for convenience as needed.

In addition, the present invention provides a method for preventing or treating cancer having cancer stem cell properties.

The method for preventing or treating cancer may include a step for inhibiting the expression or activity of epithelial membrane protein 3 (EMP3) in a subject, and, for example, may be carried out by administering the aforementioned EMP3 inhibitor to the subject.

The "cancer having cancer stem cell properties" may be cancer in which the proportion of cells, in which ALDH1 is expressed or the activity thereof is positive, is high in the total cell group constituting the cancer, for example, cancer in which the proportion of cells, in which ALDH1 is expressed or the activity thereof is positive, is 5% or greater, 10% or greater, 30% or greater, 50% or greater, or 70% or greater in the total cell group constituting the cancer.

The cancer may be one or more selected from the group consisting of lung cancer, breast cancer, liver cancer, kidney cancer, gastric cancer, pancreatic cancer, and brain cancer, but is not limited to these examples.

Furthermore, the present invention provides an epithelial membrane protein 3 (EMP3) inhibitor for use in preventing or treating cancer having cancer stem cell properties.

In still another aspect, the present invention provides a composition for assisting a radiation anticancer treatment, the composition containing an epithelial membrane protein 3 (EMP3) inhibitor as an active ingredient.

The composition according to the present invention contains an EMP3 inhibitor as an active ingredient for improving the sensitivity of cancer-related cells to radiation. The details of the EMP3 and the EMP3 inhibitor are as described above.

The cancer-related cells according to the present invention are cells constituting cancer, and may have characteristics such as a non-uniform shape, indefinite proliferation, and a weak binding force to surrounding cells compared to normal cells. Specifically, the cancer-related cells may be cancer cells or cancer stem cells, and specifically cancer stem cells.

The cancer stem cells may be undifferentiated cells having the ability to differentiate into various cancer cells, and specifically cancer cells in which ALDH1 is expressed or the activity thereof is positive. The cancer stem cells in the present invention may have characteristics that even by irradiation with radiation, cell proliferation is not inhibited, self-renewal potential is not inhibited, and migration and invasion ability are not inhibited.

Moreover, the cancer-related cells may have low sensitivity to radiation, that is, have high resistance to a radiation treatment, and may be substantially insensitive to radiation, and thus an anticancer treatment through irradiation with radiation may be impossible.

The anticancer may induce proliferation inhibition, metastasis and invasion inhibition, and cell death of cancer-related cells through irradiation with radiation, a surgical procedure, chemotherapy, or the like. The anticancer in the present invention may be the administration of the EMP3 inhibitor in combination with irradiation with radiation. When the EMP3 inhibitor is administered in combination with irradiation with radiation as described above, the sensitivity of cancer-related cells to radiation is improved by the EMP3 inhibitor, and thus the anticancer therapeutic effect by irradiation with radiation can be maximized, and cancer recurrence and metastasis can be prevented.

Further, provided is a method for enhancing the sensitivity of cancer cells to radiation, the method including a step for inhibiting the expression or activity of epithelial membrane protein 3 (EMP3) in a subject.

The cancer cells may be cancer cells including cancer stem cells, and may be, for example, cancer cells in which the proportion of cancer stem cells in a cell group constituting cancer is 5% or greater, 10% or greater, 30% or greater, 50% or greater, or 70% or greater.

Furthermore, the present invention provides an epithelial membrane protein 3 (EMP3) inhibitor for use in enhancing the sensitivity of cancer cells to radiation.

Hereinafter, the present invention will be described in detail with reference to Examples and Experimental Examples.

However, the following Examples and Experimental Examples specifically illustrate the present invention, and the contents of the present invention are not limited by e following Examples and Experimental Examples.

Production Example 1

Cell Culture and Production of Cancer Stem Cells

The human lung cancer cell line A549 obtained from American Type Culture Collection (ATCC) was cultured in an RPMI medium containing 10% fetal bovine serum and streptomycin (100 g/ml) under conditions of 37° C. and humidified 5% $CO_2$. Then, the A549 cell line cultured as described above was re-cultured in a DMEM/F12 medium containing bFGF (20 ng/ml), bEGF (20 ng/ml), and B27 stem cell supplement (1×) to transform the A549 into cancer stem cells.

Example 1

Isolation of ALDH1-Overexpressing Cancer Stem Cells and Checking of EMP3 Overexpression The A549 cells cultured in Production Example 1 were classified into ALDH1-positive cells (A549-ALDH1+) and ALDH1-negative cells (A549-ALDH1−), through the activity of ALDH1, which is a marker protein for lung cancer stem cells.

Next, gene differences between the ALDH1-positive cells and the ALDH1-negative cells were comparatively analyzed by performing gene analysis using a microarray (FIG. 1).

As a result, it was confirmed that the expression level of EMP3 genes in the ALDH1-positive cells was amplified by about 15-fold higher than in the ALDH1-negative cells.

The result indicates that EMP3 genes and ALDH1-positive lung cancer stem cells are related. In order to check the relationship, the following experiments were conducted.

Example 2

Checking of Inhibitory Effect on Sphere Formation Ability of Cancer Stem Cells
<2-1> Checking of Inhibitory Effect on Sphere Formation Ability of Cancer Stem Cells by EMP3 Antibody Treatment The A549-ALDH1$^+$ cells isolated in Example 1 were dispensed into a 25 T-flask by $5\times10^5$ cells each, and sufficiently cultured. The medium of the A549-ALDH1$^+$ cells cultured as described above was replaced with a cancer stem cell culture medium (DMEM/F12 containing bFGF (20 ng/ml), bEGF (20 ng/ml), and B27 stem cell supplement (1×)), the A549-ALDH1$^+$ cells were treated with 0.15 μg/mL of an EMP3 antibody and 0.15 μg/mL of IgG, and then cultured for 9 days, and the results thereof were checked. As the antibody against EMP3, ab236671 (Abcam, USA) was purchased and used.

The number and size of the formed spheres in the cells transformed into cancer stem cells as described above were checked using a microscope.

Figure 2:
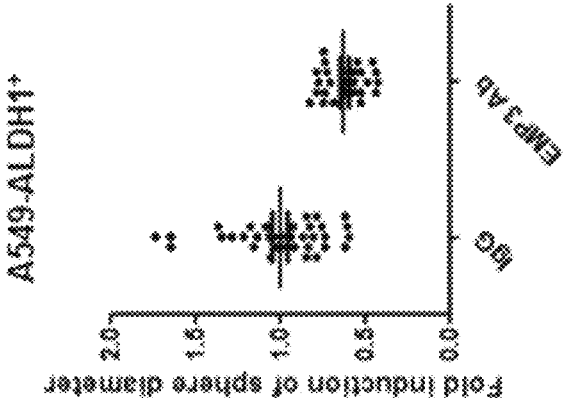
FIG. 2 is the results of checking sphere formation ability after ALDH1-positive cells are treated with an EMP3 antibody, A is the results of observing the sphere formation ability with a microscope, and B shows the results of measuring the number of the formed spheres.
Figure 2:
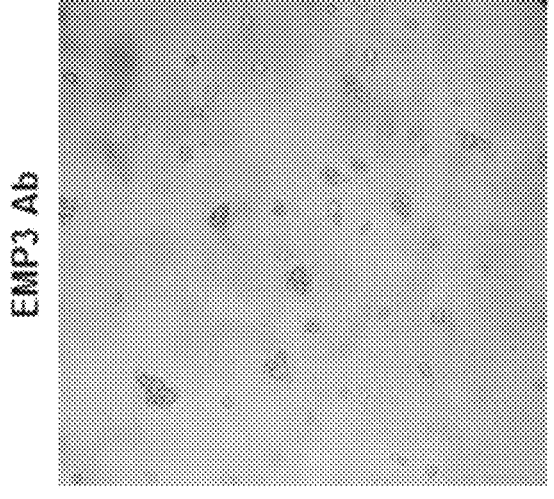
Figure 2:
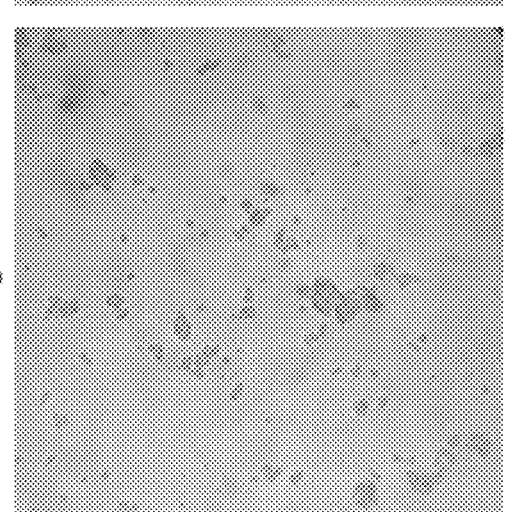

As a result, as shown in FIG. 2, it was confirmed that when the EMP3 antibody was treated, the number and size of the formed spheres were significantly reduced compared to when the EMP3 antibody was not treated.

From the above results, it can be seen that the sphere formation ability of cancer stem cells can be effectively inhibited through inhibition of EMP3 present in the cell membrane of the cancer stem cells.
<2-2> Checking of Inhibitory Effect on Sphere Formation Ability of Cancer Stem Cells by siRNA Treatment An experiment using direct gene inhibition was attempted using siRNA targeting EMP3. Accordingly, the number and size of the formed spheres in cancer stem cells were checked in the same manner as in Example <2-1>, except that the A549-ALDH1+ cells were treated with siRNA instead of the EMP3 antibody. As the siRNA, si-RNA, which was customized by BIONEER CORPORATION and in which the forward primer 5'-CUG CUU UUC GUG GCC ACU U-3' and the reverse primer 5'-AAG UGG CCA CGA AAA GCA U-3' for the EMP3 genes were each a 19-mer, was used.

Further, the changes in the expression of EMP3 and transcription factors involved in the renewal potential of cancer stem cells in the A549-ALDH1+ cells when siRNA was treated were checked using a PCR.

Figure 3A:
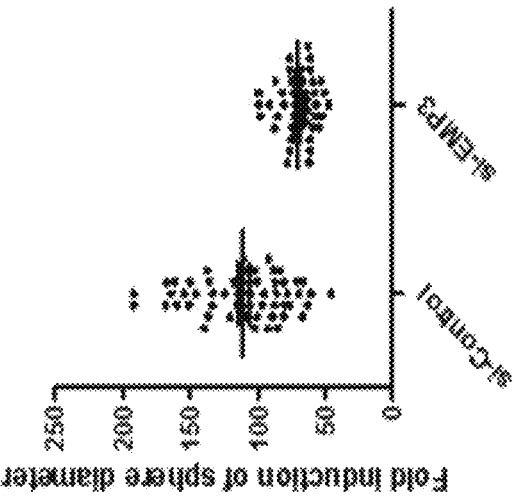
FIG. 3A shows photographs obtained by observing the sphere formation ability with a microscope, and the results of measuring the number of the formed spheres.
Figure 3A:
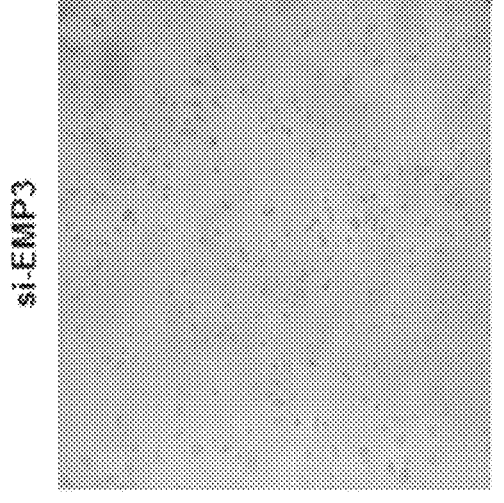
Figure 3A:
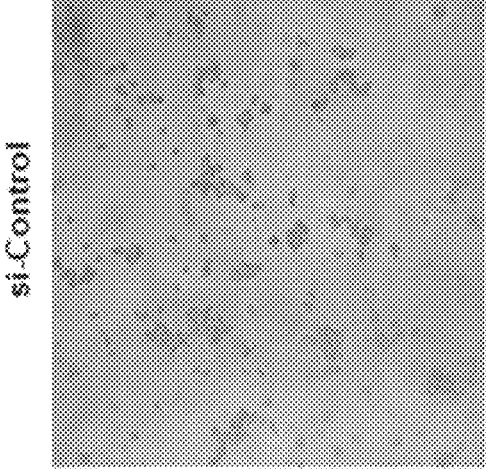

As a result, as shown in FIG. 3A, it was confirmed that the number and size of the formed spheres in the group treated with si-EMP3 were significantly reduced compared to the control group.

Figure 3B:
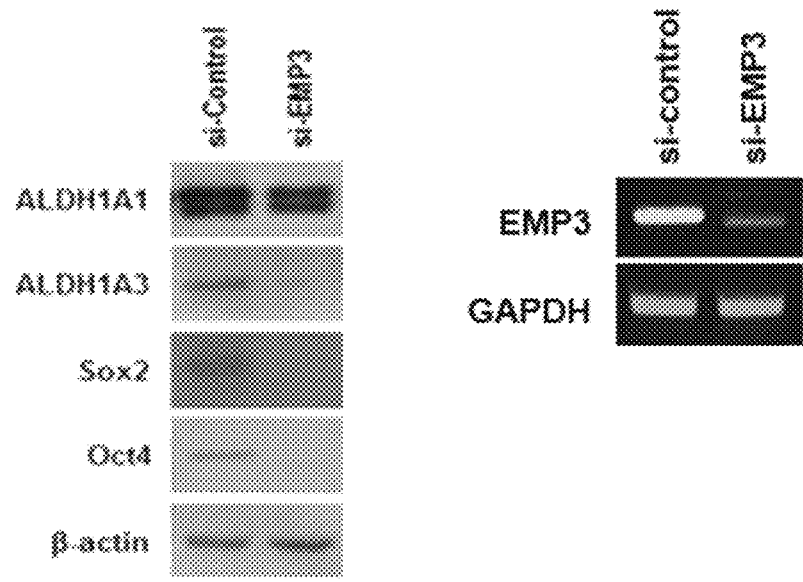
FIG. 3B shows the results of checking the expression of target genes of cancer stem cells and transcription factors involved in the renewal potential of cancer stem cells.

Moreover, as shown in FIG. 3B, it was confirmed that the expression of the target protein of the cancer stem cells was reduced. Furthermore, it was confirmed that sox2 and oct4, which are transcription factors involved in the renewal potential of cancer stem cells, were reduced.

Combining these results, it can be seen that EMP3 is involved in the formation of cancer stem cells, and can regulate transcription factors involved in the renewal potential of the cancer stem cells to inhibit the formation of the cancer stem cells.

Example 3

Checking of Inhibitory Effect on Self-Renewal Potential of Cancer Stem Cells

The A549-ALDH1$^+$ cells were dispensed one by one into a 96-well plate, and sufficiently cultured. The A549-ALDH1$^+$ cells cultured as described above were treated with 0.15 μg/mL of an EMP3 antibody and 0.15 μg/mL of IgG, and cultured for 2 weeks.

With regard to the A549-ALDH1$^+$ cancer stem cells which were treated with the EMP3 antibody or were not treated, the number of the cells present in the plate was measured using a microscope.

Figure 4:
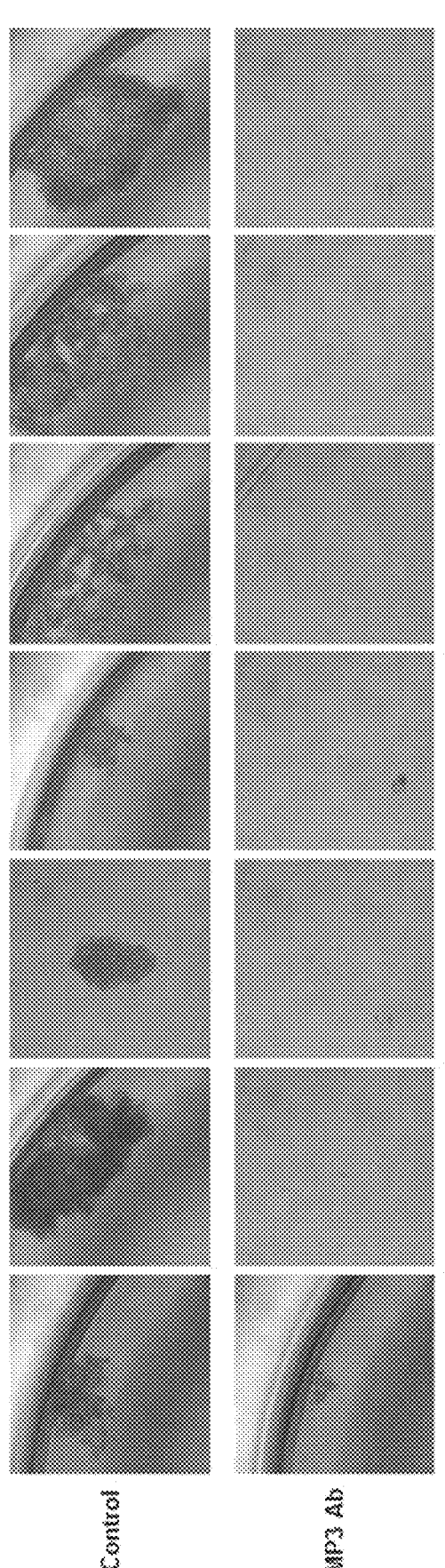
FIG. 4 is the results of checking self-renewal potential of cancer stem cells after ALDH1-positive cells are treated with an EMP3 antibody, A shows the results of microscopic observation, and B is a graph showing the number of measured cancer stem cells.
Figure 4:
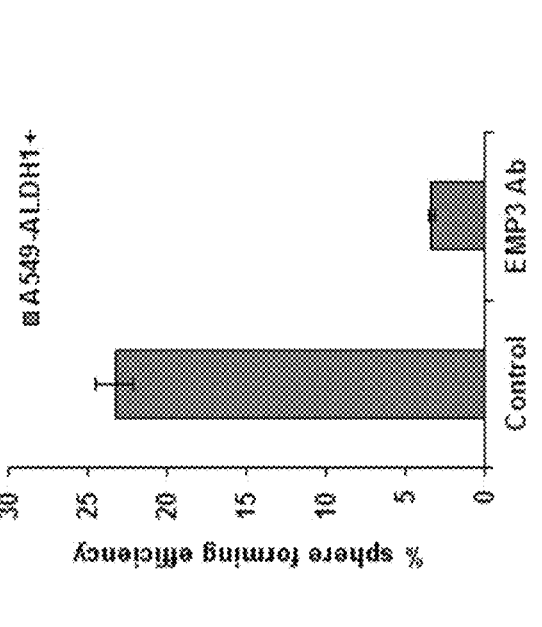

As a result, as shown in FIG. 4, it was confirmed that when the EMP3 antibody was treated, the number of the cancer stem cells was significantly reduced.

From the above results, it can be seen that the self-renewal potential, which is an inherent property of cancer stem cells, can be very effectively inhibited through inhibition of EMP3.

Example 4

Checking of Inhibitory Effect on Invasion and Migration Ability of Cancer Stem Cells
<4-1> Checking of Inhibitory Effect on Invasion and Migration Ability by EMP3 Antibody Treatment The A549-ALDH1$^+$ cancer stem cells were isolated using trypsin, $5\times10^4$ cells were each suspended in 200 μl of a nutrient medium, the nutrient medium, together with 0.15 μg/mL of an EMP3 antibody and 0.15 μg/mL of IgG, was then placed in a Transwell upper chamber having a pore size of 8 μm, 800 μl of an RPMI1640 medium containing 10% fetal bovine serum was placed in a lower chamber, and the two chambers were combined. Thereafter, the cancer stem cells were cultured in an incubator at 37° C. under a condition of 5% $CO_2$ for 48 hours. Subsequently, the membrane of the upper chamber was wiped with a cotton swab, stained with a crystal violet solution, and observed with a microscope, and then the number of cancer stem cells was measured to check the migration ability.

Moreover, the invasion analysis was performed in the same manner as in the process of checking the migration ability, except that a Transwell upper chamber coated with 10 mg/ml of a growth factor-reduced Matrigel (BD Biosciences, USA) was used.

Figure 5:
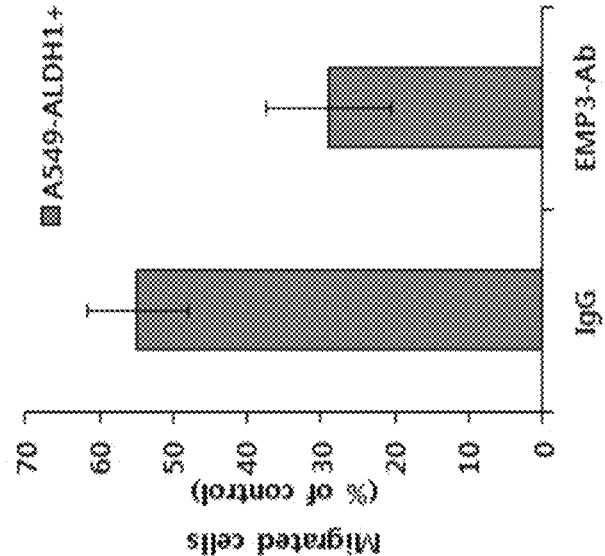
FIG. 5 shows the results of microscopic observation and a graph of the number of migrated cells, in order to check the migration ability of cancer stem cells after ALDH1-positive cells are treated with an EMP3 antibody.
Figure 5:
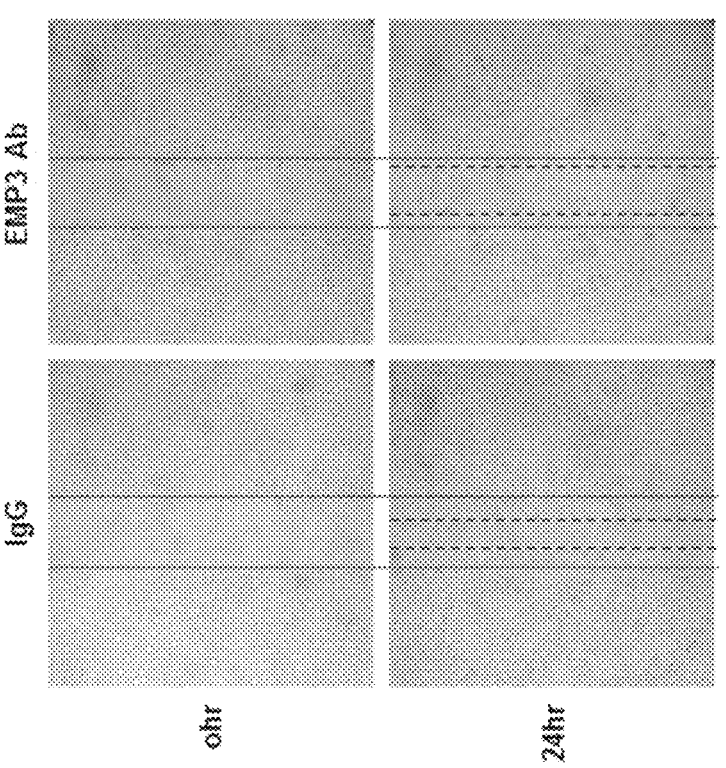
Figure 6:
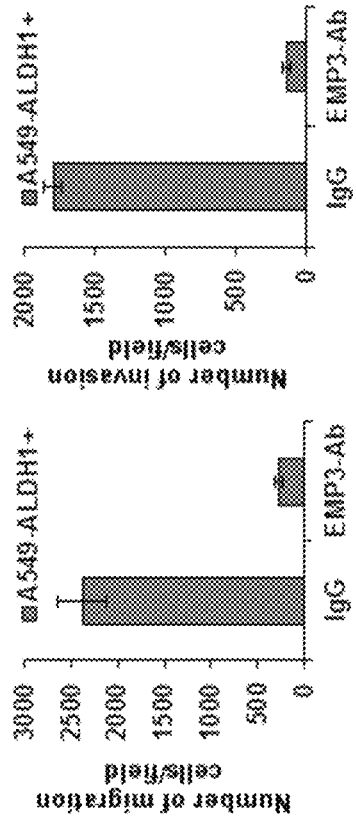
FIG. 6 shows the results of microscopic observation and a graph of the number of migrated cells, in order to check the invasiveness of cancer stem cells after ALDH1-positive cells are treated with an EMP3 antibody.
Figure 6:
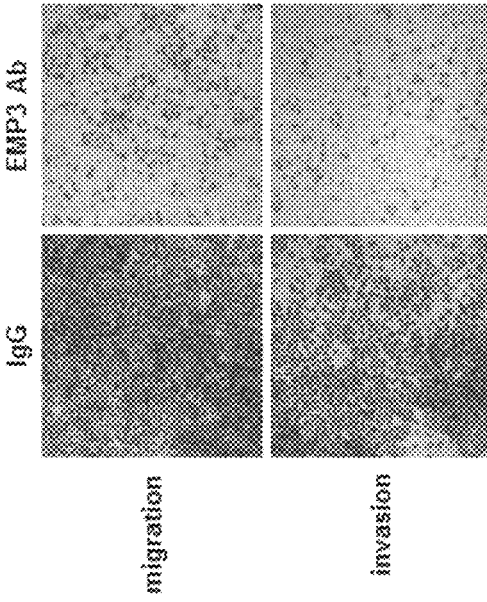

As a result, as shown in FIG. 5 and FIG. 6, it was confirmed that when the EMP3 antibody was treated, the number of cancer stem cells subjected to migration and invasion was significantly reduced compared to when the EMP3 antibody was not treated.
<4-2> Checking of Inhibitory Effect on Invasion and Migration Ability by siRNA Treatment The inhibitory effect on the invasion and migration ability of cancer stem cells by the EMP3 inhibitor treatment was checked in the same manner as in Example <4-1>, except that si-EMP3 was used instead of the EMP3 antibody.

Figure 7:
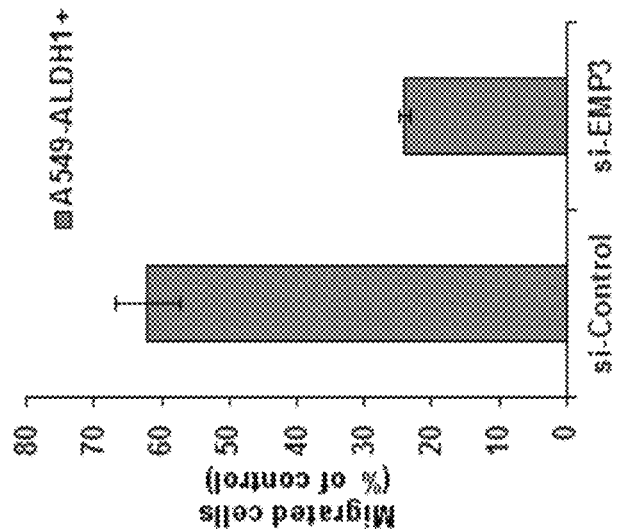
FIG. 7 shows the results of microscopic observation and a graph of the number of migrated cells, in order to check the migration ability of cancer stem cells after ALDH1-positive cells are treated with si-EMP3.
Figure 7:
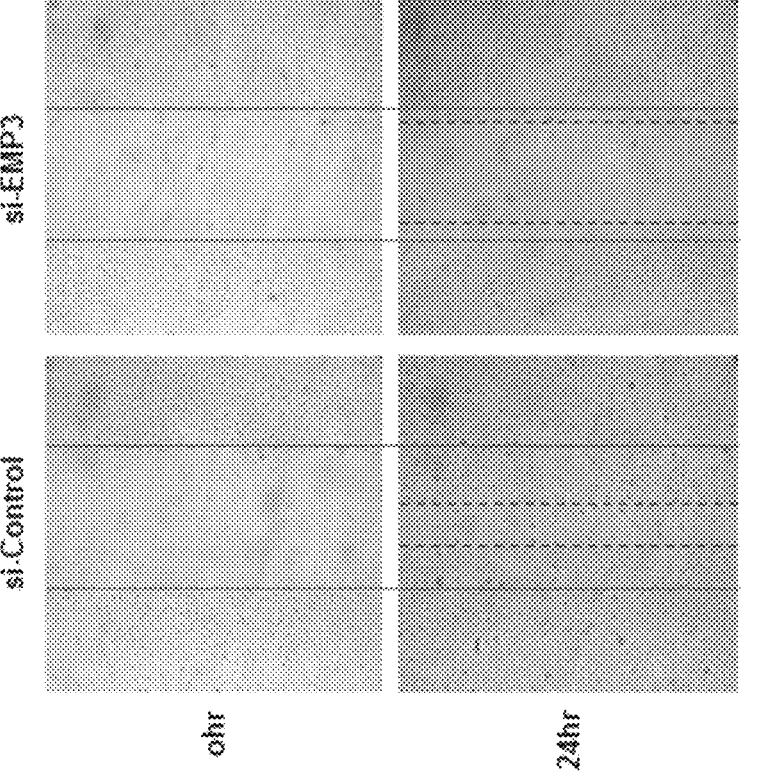
Figure 8:
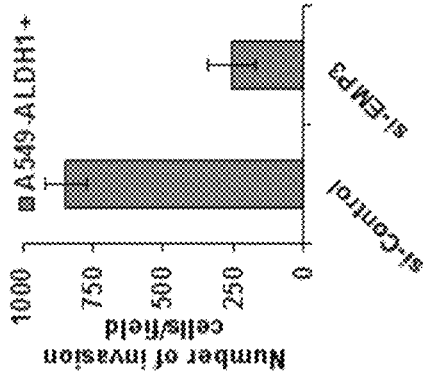
FIG. 8 shows the results of microscopic observation and a graph of the number of migrated cells, in order to check the invasiveness of cancer stem cells after ALDH1-positive cells are treated with si-EMP3.
Figure 8:
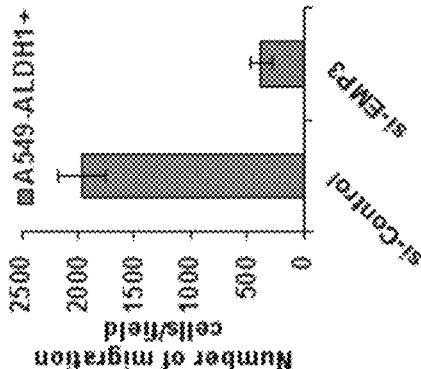
Figure 8:
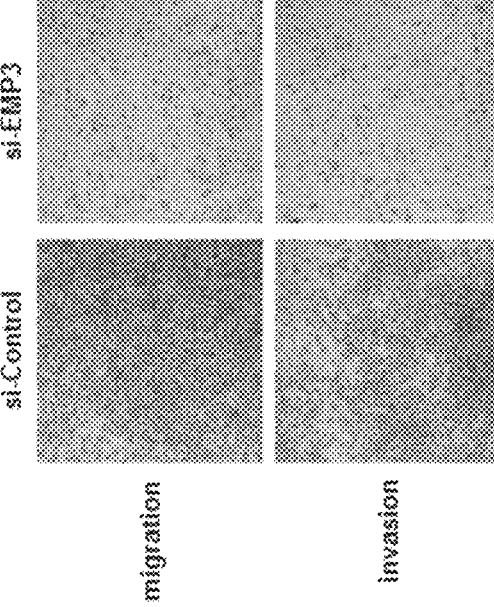

As a result, as shown in FIG. 7 and FIG. 8, it was confirmed that when the si-EMP3 was treated, the cell migration ability and invasiveness, which are characteristics of cancer stem cells, were significantly reduced.

From the above results, it can be seen that the motility of cancer stem cells is regulated by EMP3, and the migration and invasion ability of cancer stem cells can be very effectively inhibited by inhibiting EMP3.

Example 5

Checking of Inhibitory Effect on Resistance of Cancer Stem Cells to Radiation

<5-1> Checking of Inhibitory Effect on Resistance of Cancer Stem Cells to Radiation by EMP3 Antibody Treatment The A549-ALDH1$^+$ cancer stem cells were applied by $5 \times 10^2$ each to a 35-mm dish, treated with 0.15 µg/mL of an EMP3 antibody and 0.15 µg/mL of IgG one day after the application, and irradiated with radiation in a dose of 10 Gy. The treatment group irradiated with radiation was designated as an experimental group, and the group not irradiated with radiation was designated as a control group, and the cells of the experimental group and the control group were stained with a 0.5% crystal violet reagent for 10 minutes and washed several times with PBS, and then the number of colonies was measured to analyze the degree of colony formation.

Figure 9:
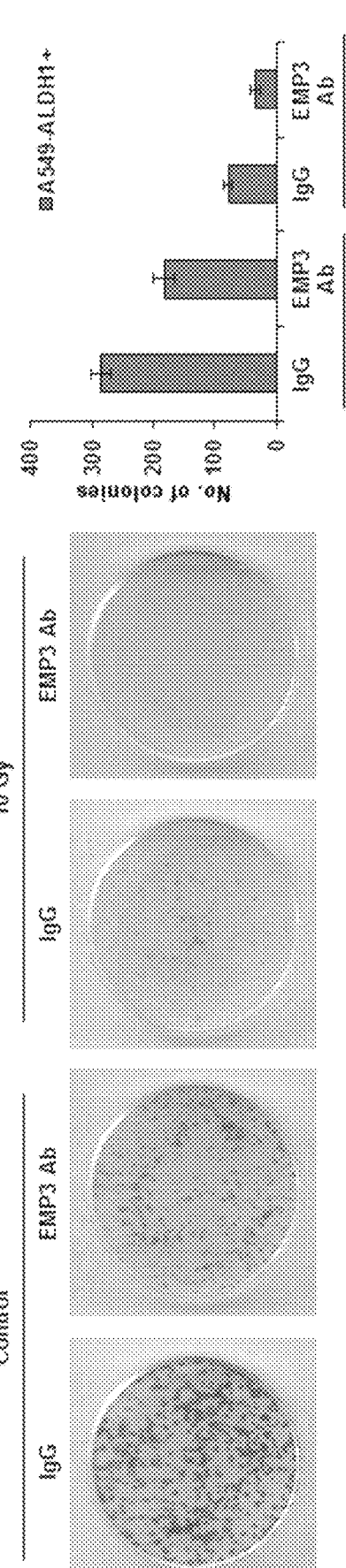
FIG. 9 shows the results of checking the resistance ability of cancer stem cells to radiation after ALDH1-positive cells are treated with an EMP3 antibody.

As a result, as shown in FIG. 9, it was confirmed that the colonies of surviving cells in the group treated with the EMP3 antibody and then irradiated with radiation were formed less than the colonies of cells surviving after irradiation with radiation without EMP3 antibody treatment.

<5-2> Checking of Inhibitory Effect on Resistance of Cancer Stem Cells to Radiation by siRNA Treatment The inhibitory effect on the resistance of cancer stem cells to radiation by EMP3 inhibitor treatment was checked in the same manner as in Example 5-1, except that si-EMP3 was used instead of the EMP3 antibody.

Figure 10:
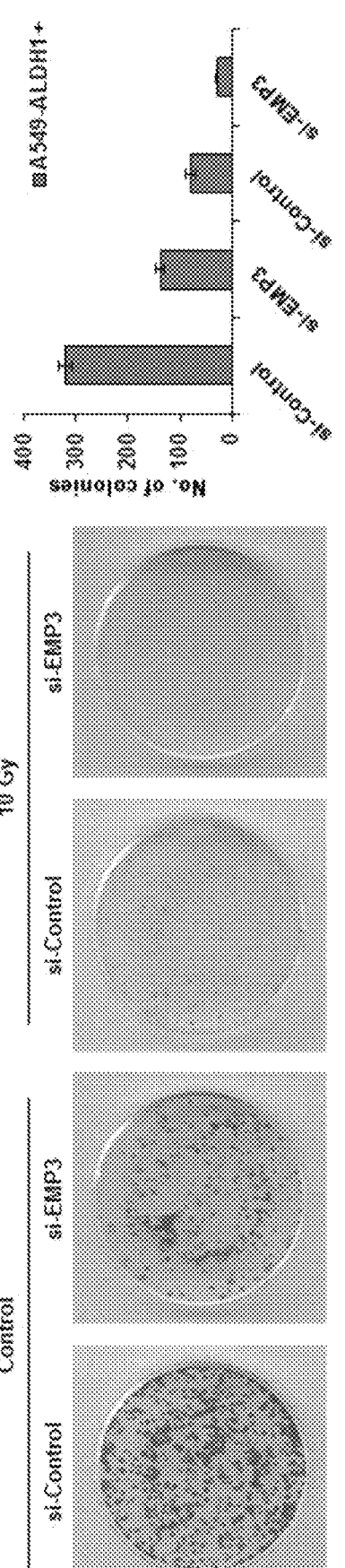
FIG. 10 shows the results of checking the resistance ability of cancer stem cells to radiation after ALDH1-positive cells are treated with si-EMP3.

As a result, as shown in FIG. 10, it was confirmed that when EMP3 was inhibited using si-EMP3, the formed colonies disappeared almost invisibly after irradiation with radiation.

From the above results, it can be seen that EMP3 can regulate the resistance ability of cancer cells, including cancer stem cells, to radiation, and EMP3 can be a target for a radiation sensitizer used in a radiation treatment.

Example 6

Survival Analysis According to EMP3 Gene Expression

In order to check that EMP3 is an important factor in the formation of cancer stem cells, the effect of EMP3 on cancer patients was checked using a data analysis program (Scientific Reports, 2018; 8:9227).

Figure 11:
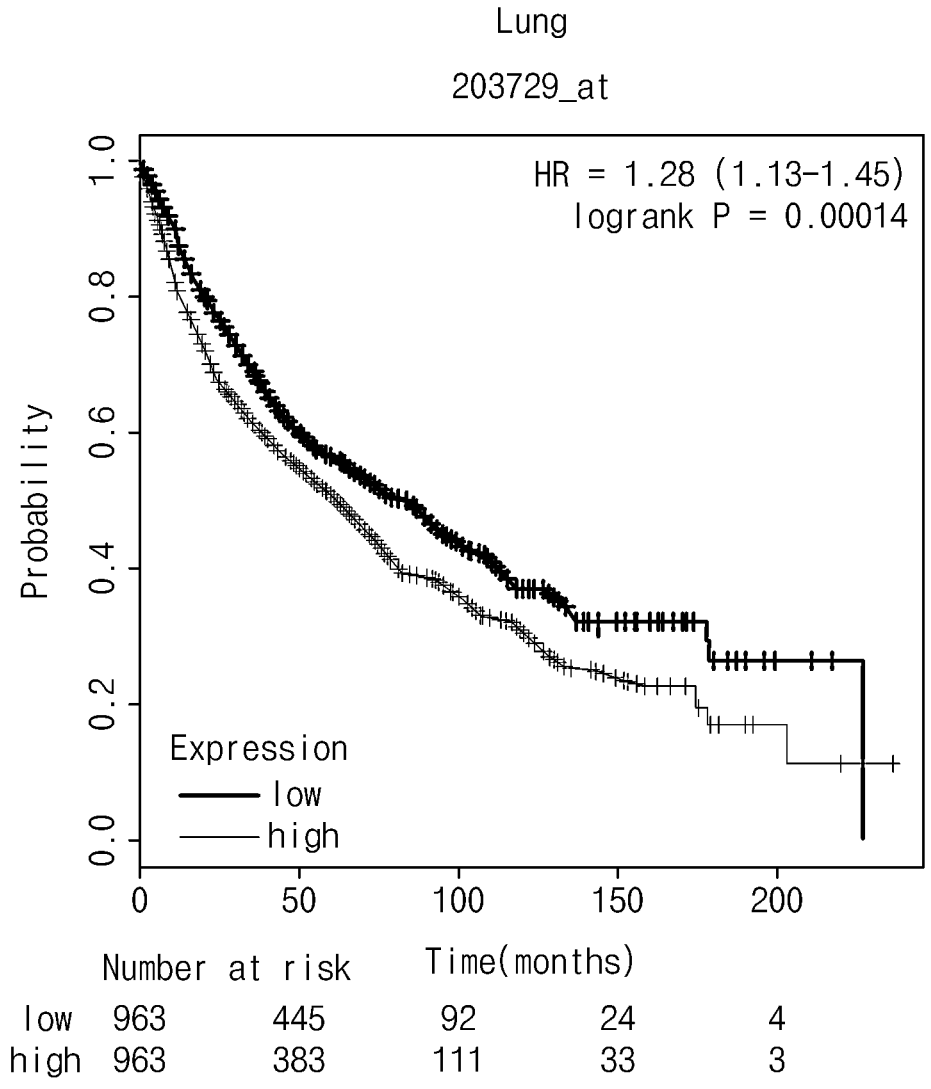
FIG. 11 shows a survival rate in a lung cancer patient group with high expression of EMP3 using the Kaplan-Meier curve.

As a result, as shown in FIG. 11, it was confirmed that the survival rate was drastically decreased in a lung cancer patient group with high expression of EMP3. From the result, it can be seen that when EMP3 is expressed, a cancer treatment may become difficult.

Hereinbefore, the present invention has been described in detail only with respect to the described embodiments, but it would be obvious to a person with ordinary skill in the art that various variations and modifications are possible within the scope of the technical idea of the present invention, and it goes without saying that such variations and modifications fall within the appended claims.

---

The invention claimed is:

1. A method for inhibiting growth of cancer stem cells, the method comprising a step of administering an epithelial membrane protein 3 (EMP3) inhibitor to a subject in need thereof,
  wherein the cancer stem cells are cancer cells in which an aldehyde dehydrogenase 1 (ALDH1) protein is over-expressed, or an activity of the ALDH1 protein is positive, wherein the ALDH1 protein is a cancer stem cell marker,
  the EMP3 inhibitor is an oligonucleotide inhibiting the expression of EMP3 genes,
  wherein the oligonucleotide inhibiting the expression of EMP3 genes is a siRNA, which is specific for EMP3 mRNA, wherein the siRNA is an oligonucleotide set forth in SEQ ID NO: 2 or SEQ ID NO: 3.

2. The method of claim 1, wherein the EMP3 inhibitor has the ability to inhibit the self-renewal potential, invasiveness, and migration ability of the cancer stem cells.

3. The method of claim 1, wherein the cancer is one or more selected from the group consisting of lung cancer, breast cancer, liver cancer, kidney cancer, gastric cancer, pancreatic cancer, and brain cancer.

4. A method for treating cancer, the method comprising a step of administering an epithelial membrane protein 3 (EMP3) inhibitor to a subject in need thereof, wherein the cancer has ALDH1-overexpressing cancer stem cell properties,
  wherein the cancer stem cells are cancer cells in which an aldehyde dehydrogenase 1 (ALDH1) protein is over-expressed, or an activity of the ALDH1 protein is positive, wherein the ALDH1 protein is a cancer stem cell marker,
  the EMP3 inhibitor is an oligonucleotide inhibiting the expression of EMP3 genes,
  wherein the oligonucleotide inhibiting the expression of EMP3 genes is a siRNA, which is specific for EMP3 mRNA, wherein the siRNA is an oligonucleotide set forth in SEQ ID NO: 2 or SEQ ID NO: 3.

5. The method of claim 4, wherein the cancer having cancer stem cell properties is cancer in which the proportion of cancer stem cells in a cell group constituting cancer is 10% or greater.

6. The method of claim 4, wherein the cancer is one or more selected from the group consisting of lung cancer, breast cancer, liver cancer, kidney cancer, gastric cancer, pancreatic cancer, and brain cancer.

7. A method for assisting a radiation anticancer treatment, the method comprising a step of administering epithelial membrane protein 3 (EMP3) inhibitor to a subject in need thereof, wherein the cancer has ALDH1-overexpressing cancer stem cell properties, the cancer stem cells are cancer cells in which an aldehyde dehydrogenase 1 (ALDH1) protein is overexpressed, or an activity of the ALDH1 protein is positive, wherein the ALDH1 protein is a cancer stem cell marker, the EMP3 inhibitor is an oligonucleotide inhibiting the expression of EMP3 genes, wherein the oligonucleotide inhibiting the expression of EMP3 genes is a siRNA, which is specific for EMP3 mRNA, wherein the siRNA is an oligonucleotide set forth in SEQ ID NO: 2 or SEQ ID NO: 3.

8. The method of claim 7, wherein the EMP3 inhibitor enhances the sensitivity of cancer cells, including cancer stem cells, to radiation.

9. The method of claim 7, wherein the cancer is one or more selected from the group consisting of lung cancer, breast cancer, liver cancer, kidney cancer, gastric cancer, pancreatic cancer, and brain cancer.

10. A method for enhancing the sensitivity of cancer cells to radiation, the method comprising a step of administering epithelial membrane protein 3 (EMP3) inhibitor to a subject in need thereof, wherein the cancer cells are cells in which an aldehyde dehydrogenase 1 (ALDH1) protein is overexpressed, or an activity of the ALDH1 protein is positive, wherein the ALDH1 protein is a cancer stem cell marker, the EMP3 inhibitor is an oligonucleotide inhibiting the expression of EMP3 genes, wherein the oligonucleotide inhibiting the expression of EMP3 genes is a siRNA, which is specific for EMP3 mRNA, wherein the siRNA is an oligonucleotide set forth in SEQ ID NO: 2 or SEQ ID NO: 3.

* * * * *

SEQUENCE LISTING

```
<160> NUMBER OF SEQ ID NOS: 4

<210> SEQ ID NO 1
<211> LENGTH: 163
<212> TYPE: PRT
<213> ORGANISM: Artificial Sequence
<220> FEATURE:
<223> OTHER INFORMATION: Synthesized

<400> SEQUENCE: 1

Met Ser Leu Leu Leu Leu Val Val Ser Ala Leu His Ile Leu Ile Leu
1               5                   10                  15

Ile Leu Leu Phe Val Ala Thr Leu Asp Lys Ser Trp Trp Thr Leu Pro
                20                  25                  30

Gly Lys Glu Ser Leu Asn Leu Trp Tyr Asp Cys Thr Trp Asn Asn Asp
            35                  40                  45

Thr Lys Thr Trp Ala Cys Ser Asn Val Ser Glu Asn Gly Trp Leu Lys
        50                  55                  60

Ala Val Gln Val Leu Met Val Leu Ser Leu Ile Leu Cys Cys Leu Ser
65                  70                  75                  80

Phe Ile Leu Phe Met Phe Gln Leu Tyr Thr Met Arg Arg Gly Gly Leu
                85                  90                  95

Phe Tyr Ala Thr Gly Leu Cys Gln Leu Cys Thr Ser Val Ala Val Phe
                100                 105                 110

Thr Gly Ala Leu Ile Tyr Ala Ile His Ala Glu Glu Ile Leu Glu Lys
            115                 120                 125

His Pro Arg Gly Gly Ser Phe Gly Tyr Cys Phe Ala Leu Ala Trp Val
        130                 135                 140

Ala Phe Pro Leu Ala Leu Val Ser Gly Ile Ile Tyr Ile His Leu Arg
145                 150                 155                 160
```

-continued

```
Lys Arg Glu

<210> SEQ ID NO 2
<211> LENGTH: 19
<212> TYPE: RNA
<213> ORGANISM: Artificial Sequence
<220> FEATURE:
<223> OTHER INFORMATION: Synthesized

<400> SEQUENCE: 2
cugcuuuucg uggccacuu                                                    19

<210> SEQ ID NO 3
<211> LENGTH: 19
<212> TYPE: RNA
<213> ORGANISM: Artificial Sequence
<220> FEATURE:
<223> OTHER INFORMATION: Synthesized

<400> SEQUENCE: 3
aaguggccac gaaaagcag                                                    19

<210> SEQ ID NO 4
<211> LENGTH: 41
<212> TYPE: PRT
<213> ORGANISM: Artificial Sequence
<220> FEATURE:
<223> OTHER INFORMATION: Synthesized

<400> SEQUENCE: 4

Asp Lys Ser Trp Trp Thr Leu Pro Gly Lys Glu Ser Leu Asn Leu Trp
1               5                   10                  15

Tyr Asp Cys Thr Trp Asn Asn Asp Thr Lys Thr Trp Ala Cys Ser Asn
            20                  25                  30

Val Ser Glu Asn Gly Trp Leu Lys Ala
        35                  40
```